United States Patent [19]

Davidson

[11] Patent Number: 5,676,632
[45] Date of Patent: Oct. 14, 1997

[54] VENTRICULAR ASSIST DEVICES OF ENHANCED HEMOCOMPATIBILITY

[75] Inventor: James A. Davidson, Germantown, Tenn.

[73] Assignee: Smith & Nephew Richards, Inc., Memphis, Tenn.

[21] Appl. No.: 469,234

[22] Filed: Jun. 6, 1995

Related U.S. Application Data

[60] Division of Ser. No. 112,599, Aug. 26, 1993, Pat. No. 5,477,864, which is a continuation-in-part of Ser. No. 36,414, Mar. 24, 1993, Pat. No. 5,509,933, which is a continuation-in-part of Ser. No. 986,280, Dec. 7, 1992, abandoned, which is a continuation-in-part of Ser. No. 647,453, Jan. 28, 1991, Pat. No. 5,169,597, which is a continuation-in-part of Ser. No. 454,181, Dec. 21, 1989, abandoned.

[51] Int. Cl.[6] .................................................. A61M 1/12
[52] U.S. Cl. .................................................. 600/16
[58] Field of Search .................................................. 600/16

[56] References Cited

U.S. PATENT DOCUMENTS

| | | |
|---|---|---|
| 2,892,706 | 6/1959 | Jafee et al. . |
| 2,987,352 | 6/1961 | Watson . |
| 3,370,946 | 2/1968 | Bertea et al. . |
| 3,408,604 | 10/1968 | Doi et al. ............... 335/216 |
| 3,643,658 | 2/1972 | Steinemann . |
| 3,677,795 | 7/1972 | Bokros et al. . |
| 3,752,664 | 8/1973 | Steinemann ............ 420/417 |
| 3,777,346 | 12/1973 | Steineman . |
| 3,849,124 | 11/1974 | Villani ................... 420/417 |
| 3,906,550 | 9/1975 | Rostoker et al. ........ 3/1.912 |
| 3,911,783 | 10/1975 | Gapp et al. ............ 420/417 |
| 4,040,129 | 8/1977 | Steinemann et al. .... 148/11.5 |
| 4,145,764 | 3/1979 | Suzuki et al. . |
| 4,170,990 | 10/1979 | Baumgart et al. ....... 606/78 |
| 4,197,643 | 4/1980 | Burstone et al. ....... 420/421 |
| 4,511,411 | 4/1985 | Brunner et al. . |
| 4,857,269 | 8/1989 | Wang et al. ............ 420/417 |
| 4,902,359 | 2/1990 | Takeuchi et al. ....... 148/133 |
| 4,969,864 | 11/1990 | Schwarzmann et al. ... 600/16 |
| 4,983,184 | 1/1991 | Steinemann ............ 623/66 |
| 5,169,597 | 12/1992 | Davidson et al. ....... 428/613 |

FOREIGN PATENT DOCUMENTS

| | | |
|---|---|---|
| 0 437 079 A1 | 12/1990 | European Pat. Off. . |
| 2703529 | 8/1978 | Germany . |

OTHER PUBLICATIONS

Zwicker, et al., Z. Metallkunde, 61 (1970) pp. 836–847.

Collings, E.W., "The Physical Metallurgy of Titanium Alloys," *American Society for Metals*, pp. 40–41, 66–70, 72–73, 120–121, 190–191, 194–195, 214–215, 218–219, 226–227 (No date).

Albert, et al., Z. Metallunde, 62 (1972) 126.

Brown & Merritt, "Evaluation of Corrosion Resistance of Biology," Case Western Reserve University, 13 Feb. 1986 (1:8).

Mears, "Electron–Probe Microanalysis of Tissue and Cells from Implant Areas," *Jnl of Bone and Joint Surgery*, vol. 48B, No. 3, pp. 576–76 (Aug. 1966).

Ferguson, Laing, and Hodge, "The Ionization of Metal Implants in Living Tissues," *Jnl of Bone and Joint Surgery*, vol. 42A, No. 1, pp. 77–90 (Jan. 1960).

(List continued on next page.)

*Primary Examiner*—William E. Kamm

[57] ABSTRACT

Ventricular assist devices fabricated from low-modulus Ti—Nb—Zr alloys to provide enhanced biocompatibility and hemocompatibility. The ventricular assist devices may be surface hardened by oxygen or nitrogen diffusion or by coating with a tightly adherent, hard, wear-resistant, hemocompatible ceramic coating. It is contemplated that the Ti—Nb—Zr alloy can be substituted as a fabrication material for any portion of a ventricular assist device that either comes into contact with blood thereby demanding high levels of hemocompatibility, or that is subject to microfretting, corrosion, or other wear and so that a low modulus metal with a corrosion-resistant, hardened surface would be desirable.

18 Claims, 3 Drawing Sheets

OTHER PUBLICATIONS

Hoar and Mears, "Corrosion–Resistant Alloys in Chloride Solutions: Materials for Surgical Implants," pp. 506–507.

Kirk–Othmer Encyclopaedia of Chemical Technology, vol. 23, pp. 98–113.

Jepson, et al., The Science & Tech., Titanium Ed. Jaffee, et al., Pergamon, N.Y., 1968, p. 677.

Heller, et al., Jour. Less Common Metals, 24 (1971) 265.

Van Noort, R., Jour. Mat. Sci., 22 (1987) 3801.

The Japan Medical Review, vol. 12, (undated) unnumbered page, pp. 12, 23.

Author Unknown, "Titanium–Niobium Base Quaternary Alloys," (Date unknown), pp. 405–419.

VENTRICULAR ASSIST DEVICES OF ENHANCED HEMOCOMPATIBILITY

RELATED APPLICATIONS

This application is a division of application Ser. No. 08/112,599, filed on Aug. 26, 1993, issued as U.S. Pat. No. 5,477,864, which is a continuation-in-part of U.S. Ser. No. 08/036,414, filed on Mar. 24, 1993, issued as U.S. Pat. No. 5,509,933, which is in turn a continuation-in-part of U.S. Ser. No. 07/986,280, filed on Dec. 7, 1992, abandoned, which is a continuation-in-part of Ser. No. 07/647,453, filed on Jan. 28, 1991, issued as U.S. Pat. No. 5,169,597, which is in turn a continuation-in-part of U.S. Ser. No. 07/454,181, filed on Dec. 21, 1989, abandoned.

BACKGROUND OF THE INVENTION

1. Field of the Invention

This invention relates to cardiovascular implants fabricated of metallic alloys of enhanced hemocompatibility that can optionally be surface hardened to provide resistance to wear, or cold-worked or cold-drawn to reduce elastic modulus, if necessary. More specifically, the invention is of ventricular assist devices fabricated of Ti—Nb—Zr alloys.

2. Description of the Related Art

Cardiovascular implants have unique blood biocompatibility requirements to ensure that the device is not rejected (as in the case of natural tissue materials for heart valves and grafts for heart transplants) or that adverse thrombogenic (clotting) or hemodynamic (blood flow) responses are avoided.

Cardiovascular implants, such as heart valves, can be fabricated from natural tissue. These bioprostheses can be affected by gradual calcification leading to the eventual stiffening and tearing of the implant.

Non-bioprosthetic implants are fabricated from materials such as pyrolytic carbon-coated graphite, pyrolytic carbon-coated titanium, stainless steel, cobalt-chrome alloys, cobalt-nickel alloys, alumina coated with polypropylene and poly-4-fluoroethylene.

For synthetic mechanical cardiovascular devices, properties such as the surface finish, flow characteristics, surface structure, charge, wear, and mechanical integrity all play a role in the ultimate success of the device. Ventricular assist devices are fabricated from various combinations of stainless steel, cobalt alloy, titanium, Ti-6Al-4V alloy, carbon fiber reinforced composites, polyurethanes, BIOLON™ (DuPont), HEMOTHANE™ (Sarns/3M), DACRON™, polysulfone, and other thermoplastics.

One of the most significant problems encountered in ventricular assist devices is the formation of blood clots (thrombogenesis). Protein coatings are sometimes employed to reduce the risk of blood clot formation. Heparin is also used as an anti-thrombogenic coating.

It has been found that stagnant flow regions in the devices or non-optimal materials contribute to the formation of blood clots. These stagnant regions can be minimized by optimizing surface smoothness and minimizing abrupt changes in the size of the cross section through which the blood flows or minimizing other flow interference aspects. While materials selection for cardiovascular implants generally is therefore dictated by a requirement for blood compatibility to avoid the formation of blood clots (thrombus), cardiovascular implants must also be designed to optimize blood flow and wear resistance.

Even beyond the limitations on materials imposed by the requirements of blood biocompatibility and limitations to designs imposed by the need to optimize blood flow, there is a need for durable designs since it is highly desirable to avoid the risk of a second surgical procedure to implant cardiovascular devices. Further, a catastrophic failure of an implanted device will almost certainly result in the death of the patient.

In the use of a ventricular assist device (VAD), the patient's heart remains in place while the VAD boosts the pumping pressure of the left ventricle of the heart. Consequently, the VAD is an assist device rather than a replacement. However, the VAD must be blood compatible.

It is also necessary that the design and materials prevent infection and thrombosis. Blood is a non-Newtonian fluid and its properties, such as viscosity, change with oxygen content, kidney function, and even the age of the patient. Further, plasma contains a suspension of fragile red blood cells which can be caught in mechanically stressful areas, thereby destroying these cells. It is therefore necessary to develop a VAD that does not stress blood components, and to fabricate the VAD from materials that are not only biocompatible, but also "blood compatible" in the sense of minimizing damage to blood components and minimizing the formation of blood clots.

There exists a need for a material that is lightweight, readily formable into complex shapes, biocompatible, and blood and tissue compatible with a hard surface that is resistant to abrasive wear, microfretting wear, and the corrosive effects of body fluids, for use in ventricular assist devices to prolong the life of mechanical components while at the same time minimizing any deleterious effect on blood components.

SUMMARY OF THE INVENTION

The invention provides cardiovascular and other medical implants of a low modulus, biocompatible, hemocompatible, metallic alloy of titanium with niobium and optionally zirconium. The invention implants include ventricular assist devices. The invention also provides surface hardened versions of these devices produced by oxygen or nitrogen diffusion hardening to improve resistance to cavitation, microfretting wear, and impact-induced wear.

The inherently low modulus of Ti—Nb—Zr alloys, between about 6 to about 12 million psi depending on metallurgical treatment and composition, provide a more flexible and forgiving construct for cardiovascular applications while improving contact stress levels, valve closure, and the ability of leaves in certain valve designs to self-align with blood flow and reduce thrombodynamic effects.

The invention provides components for use in ventricular assist devices (VADs) that are lightweight, while also being resistant to corrosive body fluids, mechanical wear, abrasive wear, and microfretting wear. Further, the components have much improved blood compatibility in the sense of reduced risk of thrombogenesis (blood clotting).

The preferred low modulus titanium alloys of the invention have the compositions: (i) titanium; about 10 wt. % to about 20 wt. % niobium; and optionally from about 0 wt. % to about 20 wt. % zirconium; and (ii) titanium; about 35 wt. % to about 50 wt. % niobium; and optionally from about 0 wt. % to about 20 wt. % zirconium. Tantalum can also be present as a substitute for Nb. These alloys are referred to herein as "Ti—Nb—Zr alloys," even though tantalum may also be present and the zirconium percentage may be zero.

The exclusion of elements besides titanium, zirconium, and niobium, or tantalum results in an alloy which does not contain known toxins or carcinogens, or elements that are known or suspected of inducing diseases or adverse tissue response in the long term.

Without the presence of zirconium in the composition, the ability of the Ti—Nb—Zr alloy to surface harden during oxygen or nitrogen diffusion hardening treatments is more limited. Therefore, presence of zirconium is especially preferred when the alloy implant must be diffusion hardened. Other non-toxic filler materials such as tantalum, which stabilize the β-phase of titanium alloy, but do not affect the low modulus, i.e., maintain it at less than about 85 GPa, could also be added.

A porous coating, such as plasma-sprayed or sintered titanium or titanium alloy (including Ti—Nb—Zr alloy) beads or wire mesh may also be added to the implant's surfaces to improve tissue attachment, such as the formation of an endothelial cell layer, preferred ventricular assist devices. Such coatings provide more favorable blood interaction and flow characteristics, and also tend to stabilize the implant with the body. Thus, such porous coatings may also be useful for connecting regions of these devices. Even though the application of such porous coatings usually requires sintering at relatively high temperatures, the properties of the Ti—Nb—Zr alloy that might affect its usefulness as an implant material are not adversely affected.

BRIEF DESCRIPTION OF THE DRAWINGS

A better understanding of the present invention can be obtained when the following detailed description of the preferred embodiments is considered in conjunction with the following drawings, in which.

DETAILED DESCRIPTION OF THE PREFERRED EMBODIMENTS

Figure 1:
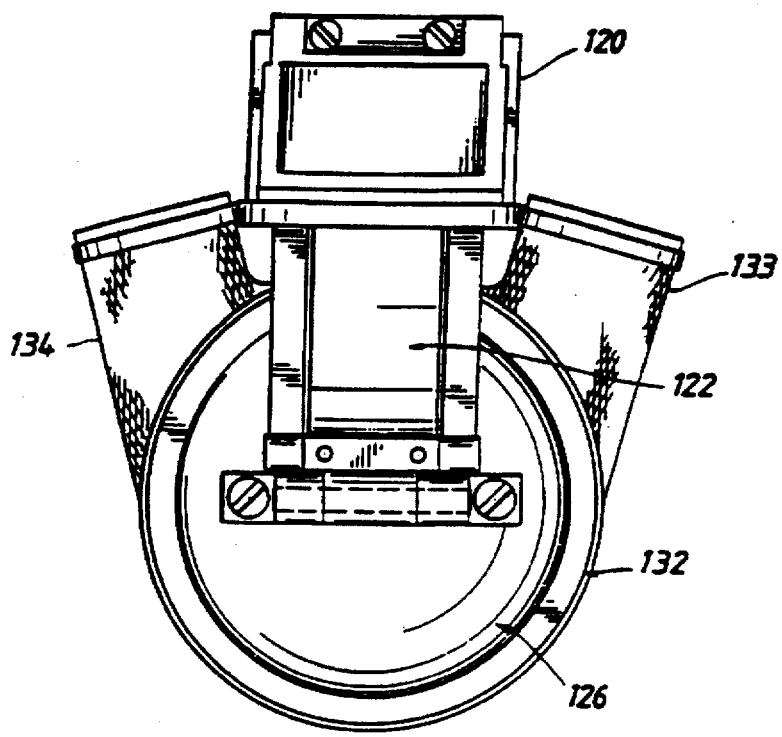
FIGS. 1A and 1B are schematic diagrams of end and front views, respectively, of a ventricular assist device.
Figure 1:
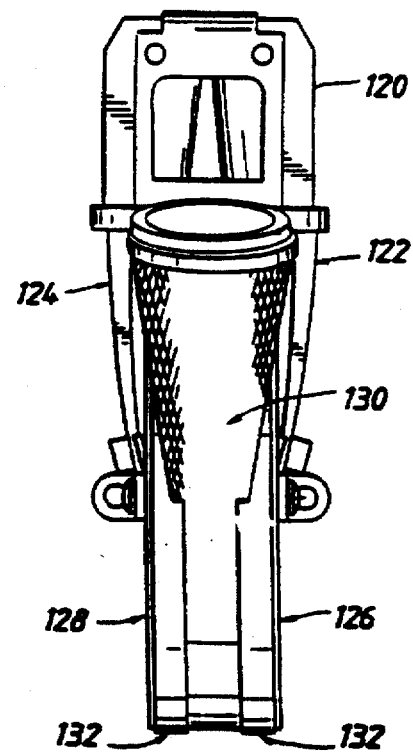

The implants of the invention are fabricated from an alloy containing titanium as a component. The preferred low modulus titanium alloys have the compositions: (i) titanium, about 10 wt. % to about 20 wt. % niobium, and optionally from about 0 wt. % to about 20 wt. % zirconium; and (ii) titanium, about 35 wt. % to about 50 wt. % niobium, and optionally from about 0 wt. % to about 20 wt. % zirconium.

In a preferred embodiment wherein the implants are surface hardened by oxygen or nitrogen diffusion, zirconium is beneficially present in amounts ranging from about 0.5 to about 20 wt. %.

Even though it is apparent that the titanium proportion of alloy used to make the invention implants could be less than 50 wt. % and the zirconium proportion zero percent, nevertheless, for the purposes of this specification, it is referred to as a "Ti—Nb—Zr alloy" or a "titanium alloy." The alloy most preferably comprises about 13 wt. % of zirconium, 13 wt. % of niobium and remainder titanium. While tantalum may be substituted for niobium to stabilize β-phase titanium, niobium is the preferred component due to its effect of lowering the elastic modulus of the alloy when present in certain specific proportions. Other elements are not deliberately added to the alloy but may be present in such quantities that occur as impurities in the commercially pure titanium, zirconium, niobium, or tantalum used to prepare the alloy and such contaminants as may arise from the alloying process.

In the specification and claims, the term "high strength" refers to an alloy having a tensile strength above at least about 620 MPa.

The term "low modulus," as used in the specification and claims, refers to a Young's modulus below about 90 GPa.

Although the hot rolled, reheated, and quenched Ti—Nb—Zr alloy is a suitable implant material, its properties can be improved by forging or other metallurgical processes or an aging heat treatment or a combination of these. Aging treatment can increase the strength and hardness of the material, and reduce its elongation while maintaining a relatively low modulus of elasticity. The treatment can be varied to obtain the desired properties. U.S. Pat. No. 5,169,597 to Davidson, et al. and U.S. Pat. No. 5,477,864, both hereby fully incorporated by reference, deals in more detail with the useful Ti—Nb—Zr alloys. Further, U.S. Ser. No. 08/036,414, hereby fully incorporated by reference, teaches how to hot work Ti—Nb—Zr alloys to produce high strength, low modulus medical implants.

It may be desirable for other reasons, such as reducing microfretting wear between mating mechanical components, to surface harden the alloy implants using oxygen or nitrogen diffusion hardening methods, or coating with a hard wear resistant coating. In the latter event, the surface of the implant may be coated with an amorphous diamond-like carbon coating or ceramic-like coating such as zirconium or titanium oxide, zirconium or titanium nitride, or zirconium or titanium carbide using chemical or plasma vapor deposition techniques to provide a hard, impervious, smooth surface coating. These coatings are especially useful if the implant is subjected to conditions of wear, such as, for instance, in the case of mating parts in ventricular assist devices.

Methods for providing hard, low-friction, impervious, biocompatible amorphous diamond-like carbon coatings are known in the art and are disclosed in, for example, EPO patent application 302 717 A1 to Ion Tech and Chemical Abstract 43655P, Vol. 101, describing Japan Kokai 59/851 to Sumitomo Electric, all of which are incorporated by reference herein as though full set forth.

Figure 2:
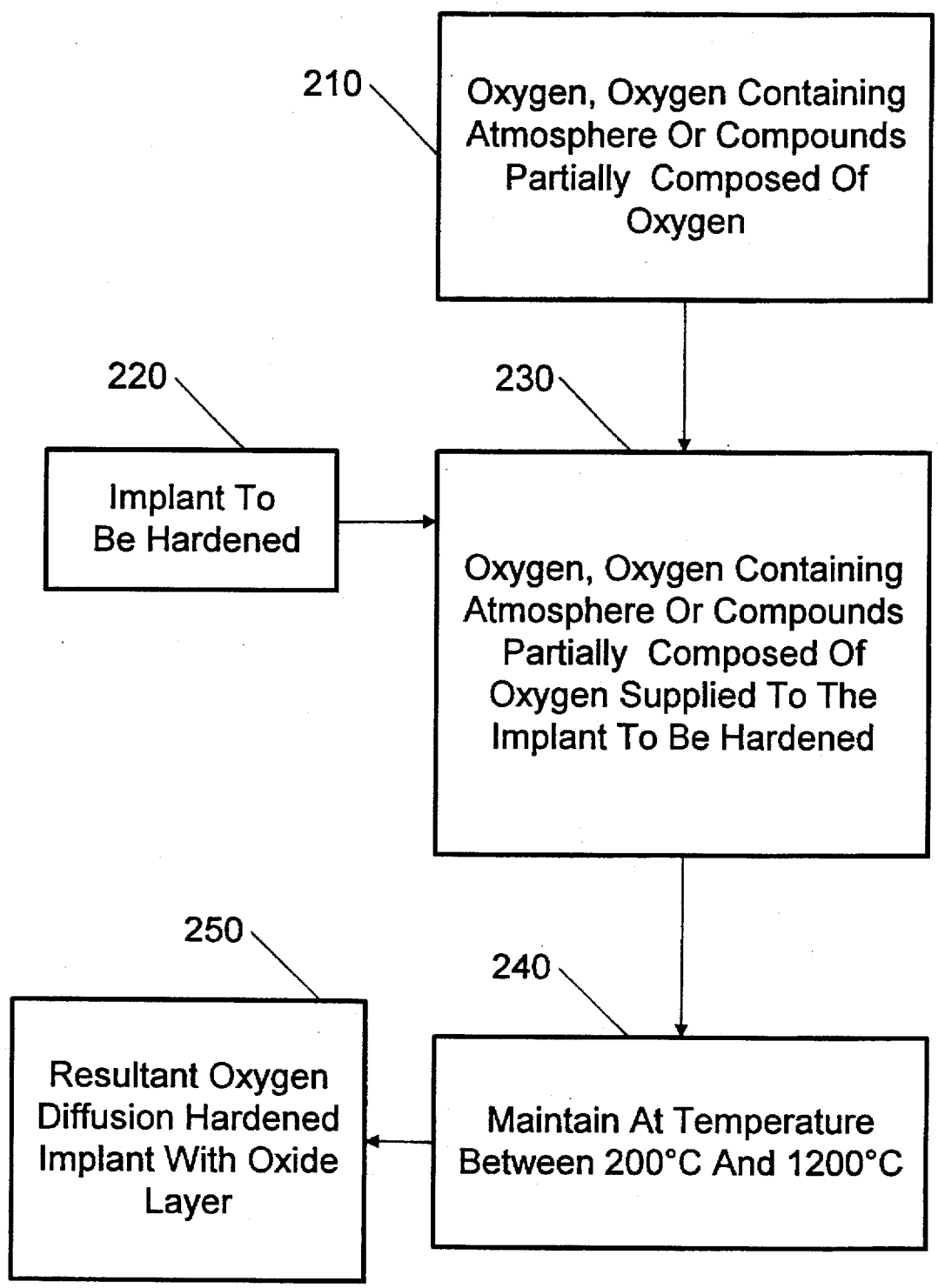
FIG. 2 is a schematic diagram illustrating the oxygen diffusion hardening method for forming an oxide-containing hardened layer on a portion of a implant, e.g. a ventricular assist device.

A preferred process for oxygen diffusion hardening is described in U.S. Pat. 5,372,560, filed on the same day as this patent application, which is hereby fully incorporated by reference. Referring to FIG. 2, oxygen diffusion hardening according to this process requires the supply of oxygen, or an oxygen containing atmosphere, or compounds partially composed of oxygen, such as water (steam), carbon dioxide, nitrogen dioxide, sulfur dioxide, and the like at 210. These substances are supplied to the implant to be hardened 220 at 230 which is maintained at a temperature preferably between 200° C. and 1200° C. at 240. The amount of time required at a given temperature to effectively produce the surface and near-surface hardened implants at 250 is related exponentially, by an Arhennius-type relationship to the temperature. That is, shorter periods of time are required at higher temperatures for effective diffusion hardening. The resultant oxygen diffusion hardened implants at 250 are characterized in that the oxide film contains primarily a mixture of titanium and zirconium oxides in the implant surface. Niobium oxides may also be present. Immediately underlying this mixed-oxide film is sometimes a region of oxygen-rich metal alloy. Underlying the sometimes-obtained oxygen-rich alloy layer is the core Ti—Nb—Zr alloy. The interface between the sometimes-obtained oxygen-rich alloy layer and the oxide regions is typically zirconium-rich in comparison to the underlying Ti—Nb—Zr alloy. In a most preferred embodiment, the Ti—Nb—Zr alloy is subjected to temperature and an environment of argon gas that has been moisturized by bubbling through a water bath. The water vapor disassociates at the implant surface to produce oxygen which diffuses into the implant to produce the desired hardened surface.

Figure 3:
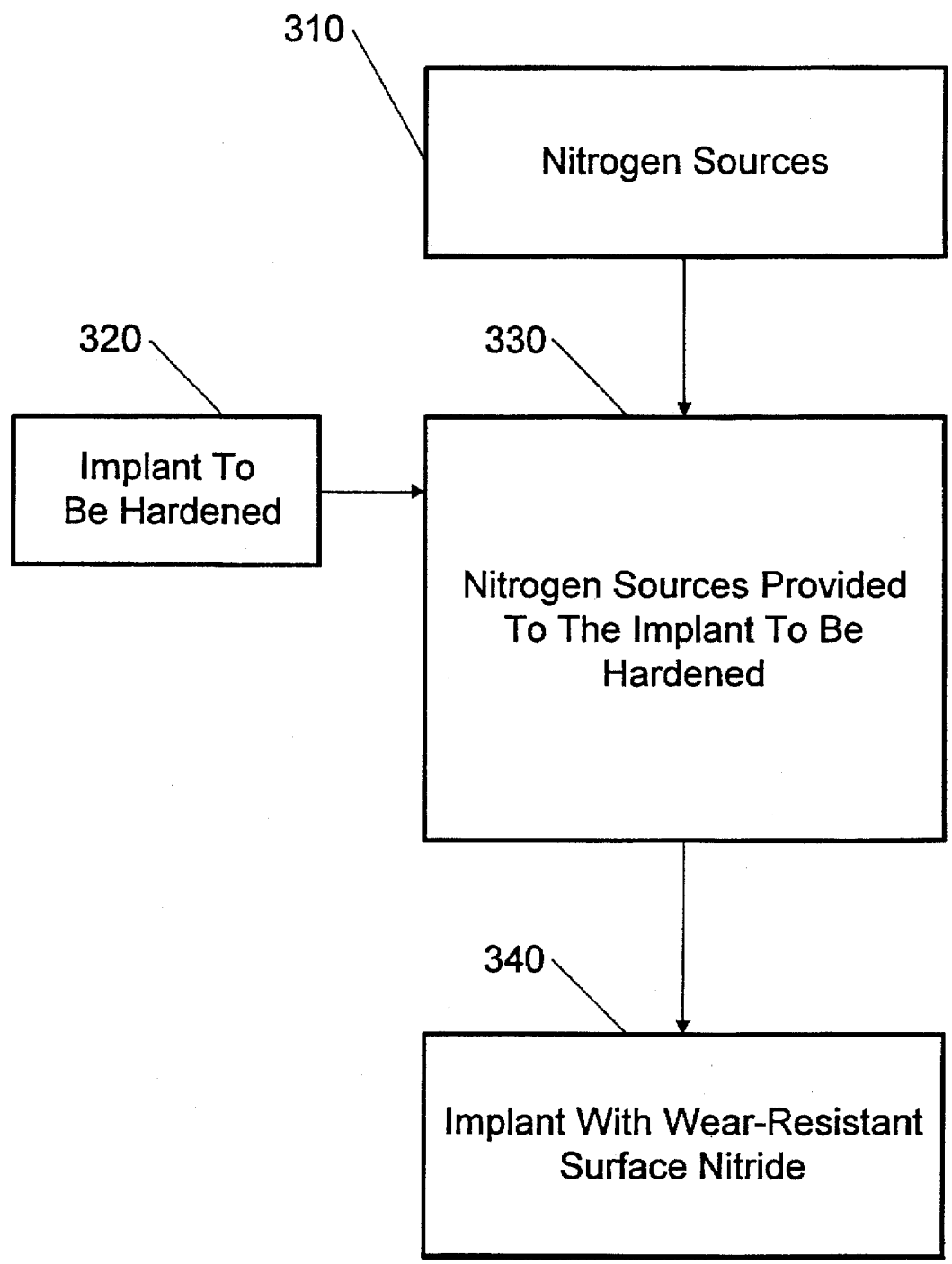
FIG. 3 is a schematic diagram illustrating the nitrogen diffusion hardening method of forming a nitride-containing hardened layer on a portion of an implant, e.g. a ventricular assist device.

Referring to FIG. 3, nitrogen diffusion processes can also be utilized in which nitrogen sources 310 are provided to the implant to be hardened 320 instead of oxygen, at 330. These nitrogen diffusion surface hardening processes will tend to harden the metal alloy substrate in a similar manner to that of oxygen diffusion hardening or conventional oxygen hardening (which is also useful), and produce a yellow-orange insulative, wear-resistant surface oxide nitride layer on the implant at 340 instead of the blue-black surface oxide which typically forms from the in situ oxygen diffusion hardening process.

Implants fabricated from the inventive alloy may be supplied with a porous bead or wire coating of titanium alloy of the same or different composition including pure titanium to allow endothelial cell attachment to blood-contacting flow surfaces or for stabilization of the implant in the body of the patient after implantation by tissue ingrowth into the porous structure. Such porous structures are normally attached to the implant surface by sintering or plasma spraying. Sintering involves heating the implant to above about 1250° C. The mechanical properties of titanium alloys can change significantly due to substantial grain growth and other metallurgical factors arising from the sintering process. Thus, after sintering to attach the porous coating, it may be desirable in some instances to reheat the Ti—Nb—Zr implant, for example, to about 875° C. (or above the β-transus) for 20–40 minutes then water quench before aging at about 500° C. for about 6 hours to restore mechanical properties. If quenched adequately from the sintering temperature, it may be possible to go directly to the aging process. An alternative method of attaching a porous coating is to simply plasma spray metal powder or micro-beads onto the implant's surface after appropriate mechanical and thermal treatments.

Further, the implants of the invention may optionally be surface coated with medicaments such as anti-inflammatory agents, anti-thrombus agents, antibiotics, proteins that reduce platelet adhesion, and the like to improve their acceptability in a living body.

Ventricular Assist Devices

The Novacor designed VAD illustrated in FIGS. 1A and 1B have a solenoid mechanism 120 which sends energy through beam-springs 122, 124 that extend to the back of pump pusher plates 126, 128. The energy stored in the springs translates into linear motion of the plates which exerts force on the flexible blood sac 130. The blood sac 130 consists of a butyl rubber layer sandwiched between two layers of polyurethane Biomer. The blood sac 130 is supported within a cylindrical aluminum ring 132 that acts as a pump housing. The blood inflow 133 and outflow 134 ports are positioned tangentially on opposite sides of the housing to ensure straight-through blood flow. The ports are formed of an epoxy-impregnated Kevlar fabric shell that is integrated into the housing. The ports also encapsulate trileaflet inlet and outlet valves made from bovine pericardium tissue.

When implanted into the body, fittings for attaching inflow and outflow valves to vascular conduits are bonded to a pump bulkhead, not shown, which also provides the framework for an encapsulating shell around the pump. This encapsulating shell also has provision for mounting the solenoid energy converter. The solenoid energy converter consists of two solenoid mechanisms, two lightweight titanium beam-springs, and an aluminum support structure. All of these metallic components would come into contact with blood components and body tissue. Therefore, the invention proposes that the titanium beam-springs be replaced with beam-springs of Ti—Nb—Zr alloy. Further, the aluminum support structure would likewise be replaced with a Ti—Nb—Zr alloy support structure that may optionally be hardened and/or coated with a hard coating.

Novacor has identified, in designing the solenoid, that "the challenge was coming up with something that would run for 100 million cycles a year, without requiring maintenance." O'Connor, Lee, "Novacor's VAD: How to Mend a Broken Heart," Mechan. Engr'g pp. 53–55 (November 1991). The invention components fabricated from Ti—Nb—Zr alloys then hardened or coated with hard, wear resistant coatings provide surfaces that are hard, microfretting wear resistant, biocompatible and blood compatible so that they would meet this goal. To further reduce friction and wear of wear surfaces of implant devices, a thin boron or silver surface layer can be applied as an overlay on the previously diffusion hardened Ti—Nb—Zr surface.

The Hardened Surfaces

The oxygen or nitrogen diffusion hardened surface of the alloy implants may be highly polished to a mirror finish to further improve blood flow characteristics. Further, the oxide- or nitride-coated surfaces maybe coated with substances that enhance biocompatibility and performance. For example, a coating of phosphatidyl choline, heparin, or other proteins to reduce platelet adhesion to the surfaces of the implant, or the use of antibiotic coatings to minimize the potential for infection. Boronated or silver-doped hardened surface layers on the implant reduces friction and wear between contacting parts of ventricular assist devices. Additionally, amorphous diamond-like carbon, pyrolyric carbon, or other hard ceramic surface layers can also be coated onto the diffusion hardened surface to optimize other friction and wear aspects. The preferred diffusion hardened surface layer described in this application provides a hard, well-attached layer to which these additional hard coatings can be applied with a closer match between substrate and coating with respect to hardness. Other, conventional methods of oxygen surface hardening are also useful. Nitriding of the substrate leads to a hardened nitride surface layer. Methods of nitridation known in the art may be used to achieve a hard nitride layer.

Regardless of how a Ti—Nb—Zr alloy implant's surface is hardened, the friction and wear (tribiological) aspects of the surface can be further improved by employing the use of silver doping or boronation techniques. Ion-beam-assisted deposition of silver films onto ceramic surfaces can improve tribiological behavior. The deposition of up to about 3 microns thick silver films can be performed at room temperature in a vacuum chamber equipped with an electron-beam hard silver evaporation source. A mixture of argon and oxygen gas is fed through the ion source to create an ion flux. One set of acceptable silver deposition parameters consists of an acceleration voltage of 1 kev with an ion current density of 25 microamps per $cm^2$. The silver film can be completely deposited by this ion bombardment or formed partially via bombardment while the remaining thickness is achieved by vacuum evaporation. Ion bombardment improves the attachment of the silver film to the Ti—Nb—Zr alloy substrate. Similar deposition of silver films on existing metal cardiovascular implants may also be performed to improve tribological behavior, as well as antibacterial response.

An alternate method to further improve the tribological behavior of Ti—Nb—Zr alloy surfaces of cardiovascular implants is to apply boronation treatments to these surfaces such as commercial available boride vapor deposition, boron ion implantation or sputter deposition using standard ion implantation and evaporation methods, or form a boron-type coating spontaneously in air. Boric Acid ($H_3BO_3$) surface films provide a self-replenishing solid lubricant which can further reduce the friction and wear of the ceramic substrate. These films form from the reaction of the $B_2O_3$ surface (deposited by various conventional methods) on the metal surface with water in the body to form lubricous boric acid. Conventional methods that can be used to deposit either a boron (B), $H_3BO_3$, or $B_2O_3$ surface layer on the cardiovascular implant surface include vacuum evaporation (with or without ion bombardment) or simple oven curing of a thin layer over the implant surface. The self-lubricating mechanism of $H_3BO_3$ is governed by its unique layered, triclinic crystal structure which allows sheets of atoms to easily slide over each other during articulation, thus minimizing substrate wear and friction.

Additionally, surfaces (metal or coated) of all the cardiovascular and medical implants discussed may optionally be coated with agents to further improve biological response. These agents include anticoagulants, proteins, antimicrobial agents, antibiotics, and the like medicaments.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. In a ventricular assist device for implantation in living body tissue of a patient of the type comprising:
   (a) a pump to increase the pumping pressure of a left ventricle of a patient's heart; and
   (b) a solenoid energy converter to provide energy to the pump;
   said pump and solenoid energy converter having surfaces that are exposed to body tissue and body fluid when the ventricular assist device is in use,
   the improvement wherein at least a portion of the ventricular assist device is
   fabricated from a metal alloy with enhanced hemocompatibility, said alloy comprising:
      (i) titanium; and
      (ii) from about 10 to about 20 wt. % niobium or from about 35 to about 50 wt % niobium;
   wherein the alloy is free of deliberately added toxic elements.

2. The improved ventricular assist device of claim 1, wherein at least a portion of the titanium is β-phase titanium and said alloy further comprises an amount of zirconium sufficient to retard the transformation of β-phase titanium.

3. The ventricular assist device of claim 2, wherein the metal alloy comprises from about 0.5 to about 20 wt. % zirconium.

4. The improved ventricular assist device of claim 2, further comprising a hardened outer surface layer on at least a portion of the ventricular assist device, said layer selected from the group consisting of oxide-containing layers formed by oxygen diffusion hardening and nitride-containing layers formed by nitrogen diffusion hardening.

5. The improved ventricular assist device of claim 2, wherein the metal alloy comprises about 13 wt. % niobium, about 13 wt. % zirconium and remainder titanium.

6. The improved ventricular assist device of claim 2, wherein the amount of zirconium sufficient to retard the transformation of β-phase titanium is less than about 20 wt. % zirconium.

7. The improved ventricular assist device of claim 1, further comprising a hardened outer surface layer on at least a portion of the ventricular assist device, said layer selected from the group consisting of oxide-containing layers formed by oxygen diffusion hardening and nitride-containing layers formed by nitrogen diffusion hardening.

8. The improved ventricular assist device of claim 1 or claim 2 or claim 7 or claim 4, wherein the surfaces of the ventricular assist device that are exposed to body tissue and body fluid are at least partially coated with a composition selected from the group consisting of anticoagulants, antimicrobial agents, antibiotics, and medicaments.

9. The improved ventricular assist device of claim 1 or claim 2 or claim 7 or claim 4, further comprising low friction wear-resistant outer surface silver-containing layer on at least a portion of the ventricular assist device.

10. The improved ventricular assist device of claim 1 or claim 2 or claim 7 or claim 4, further including a low friction wear-resistant outer surface boron-containing layer on at least a portion of the ventricular assist device.

11. In a ventricular assist device for implantation in living body tissue of a patient of the type comprising:
   (a) a pump to increase the pumping pressure of a left ventricle of a patient's heart; and
   (b) a solenoid energy converter to provide energy to the pump,
   said pump and solenoid energy converter having surfaces that are exposed to body tissue and body fluid when the ventricular assist device is in use,
   the improvement wherein at least a portion of the ventricular assist device is:
      fabricated from a metal alloy with enhanced hemocompatibility, said alloy comprising:
         (i) titanium; and
         (ii) niobium and gantalum, wherein the combined wt. % of niobium and tantalum is from about 10 to about 20 wt. % or from about 35 to about 50 wt. %;
      wherein the alloy is free of deliberately added toxic elements.

12. The improved ventricular assist device of claim 11, wherein at least a portion of the titanium is β-phase titanium and said alloy further comprises an amount of zirconium sufficient to retard the transformation of β-phase titanium.

13. The ventricular assist device of claim 12, wherein the metal alloy comprises from about 0.5 to about 20 wt. % zirconium.

14. The improved ventricular assist device of claim 12; further comprising a hardened outer surface layer on at least a portion of the ventricular assist device, said layer selected from the group consisting of oxide-containing layers formed by oxygen diffusion hardening and nitride-containing layers formed by nitrogen diffusion hardening.

15. The improved ventricular assist device of claim 11, further comprising a hardened outer surface layer on at least a portion of the ventricular assist device, said layer selected from the selected form the group consisting of oxide-containing layers formed by oxygen diffusion hardening and nitride-containing layers formed by nitrogen diffusion hardening.

16. The improved ventricular assist device of claim 11 or claim 12 or claim 15 or claim 14, wherein the surfaces of the ventricular assist device that are exposed to body tissue and body fluid are at least partially coated with a composition selected from the group consisting of anticoagulants, antimicrobial agents, antibiotics, and medicaments.

17. The improved ventricular assist device of claim 11 or claim 12 or claim 15 or claim 14, further comprising a low friction wear-resistant outer surface silver-containing layer on at least a portion of the ventricular assist device.

18. The improved ventricular assist device of claim 11 or claim 12 or claim 15 or claim 14, further including a low friction wear-resistant outer surface boron-containing layer on at least a portion of the ventricular assist device.

* * * * *